United States Patent [19]

Kornberg

[11] Patent Number: 4,969,877
[45] Date of Patent: Nov. 13, 1990

[54] SYRINGE

[75] Inventor: Elliot Kornberg, Cocoa Beach, Fla.

[73] Assignee: The Pascall Medical Corporation, Cocoa Beach, Fla.

[21] Appl. No.: 436,688

[22] Filed: Nov. 15, 1989

Related U.S. Application Data

[62] Division of Ser. No. 259,709, Oct. 19, 1988, Pat. No. 4,915,699.

[51] Int. Cl.⁵ .............................................. A61M 5/32
[52] U.S. Cl. .................................... 604/195; 604/198
[58] Field of Search ............... 604/195, 198, 187, 232, 604/263

[56] References Cited

U.S. PATENT DOCUMENTS

| | | |
|---|---|---|
| 2,880,725 | 4/1959 | Kendall . |
| 2,888,923 | 6/1959 | Reis . |
| 2,935,067 | 4/1960 | Douet . |
| 3,584,626 | 6/1971 | Johansson . |
| 4,405,322 | 9/1983 | Jessup .................................. 604/232 |
| 4,507,117 | 3/1985 | Vining et al. . |
| 4,631,057 | 12/1986 | Mitchell . |
| 4,639,249 | 1/1987 | Larson . |
| 4,643,199 | 1/1987 | Jennings, Jr. et al. . |
| 4,650,468 | 3/1987 | Jennings, Jr. . |
| 4,675,005 | 6/1987 | Deluccia . |
| 4,692,156 | 9/1987 | Haller . |
| 4,710,170 | 12/1987 | Haber et al. . |
| 4,723,945 | 2/1988 | Theiling ................................ 604/232 |
| 4,767,413 | 8/1988 | Haber et al. . |
| 4,840,619 | 9/1989 | Hughes ................................ 604/198 |

Primary Examiner—John D. Yasko
Attorney, Agent, or Firm—Beveridge, DeGrandi & Weilacher

[57] ABSTRACT

A syringe assembly which greatly reduces the chances of an operator coming in contact with an infectious needle. The syringe assembly includes an outer casing within which an inner chamber slides. A plunger having a sealing plug at one end extends into both the inner chamber and outer casing such that the sealing plug is fixedly secured within the interior of the inner chamber and outer casing, yet free to slide along the length of the inner chamber. The inner chamber and outer casing are structured such that the needle can be retracted completely within the interior of the outer casing when the inner chamber is releasably locked at the rear end of the outer casing. The needle can also be placed into an operational position when the inner chamber with attached needle is releasably locked at the forefront of the outer casing. The releasable locking of the inner chamber to the outer casing at the forward and rearward ends of the outer casing is achieved by either utilizing frictional contact between the two which is greater than that between the inner chamber and sealing plug. In an alternative embodiment, a knob/groove or ridge/groove locking arrangement is used. The releasable locking arrangement relied on are such that by simply pushing the plunger forward or rearward, the needle can be retracted or placed in oprative position without the requirement for complicated alignment and twisting operations.

24 Claims, 5 Drawing Sheets

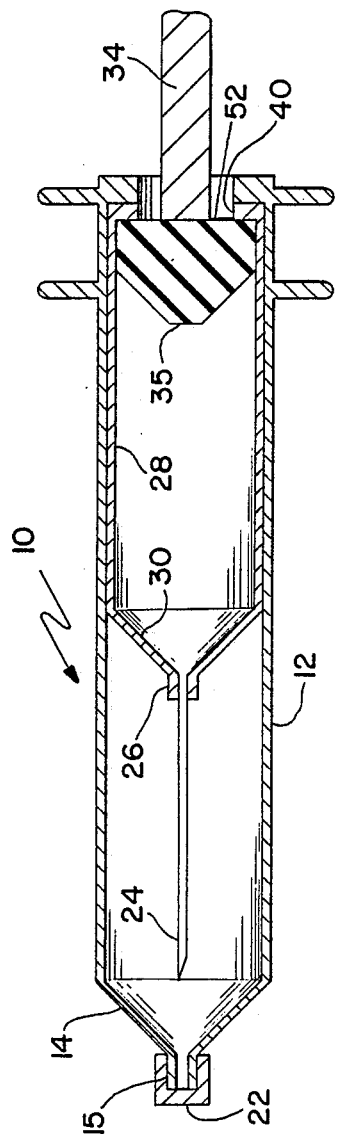
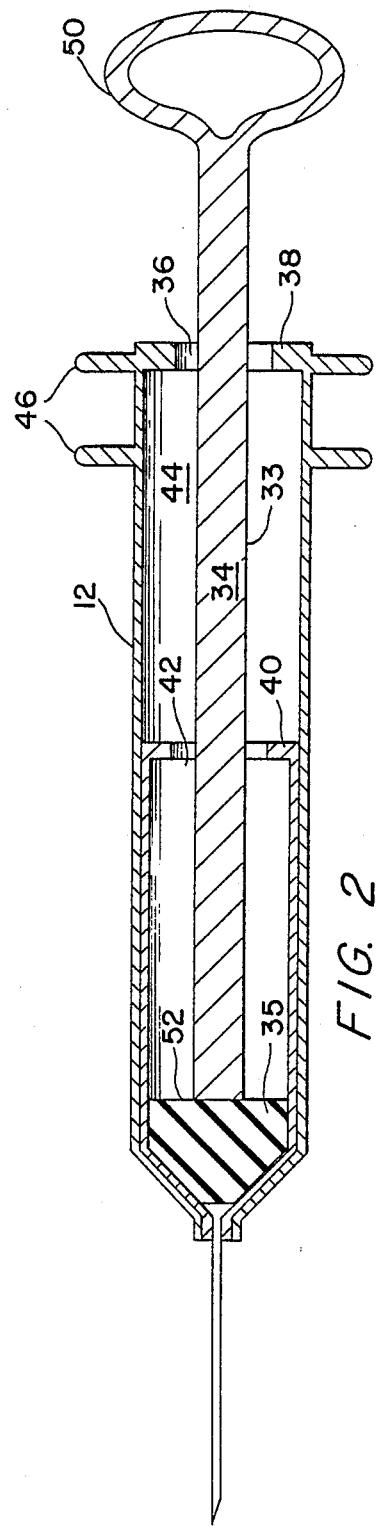

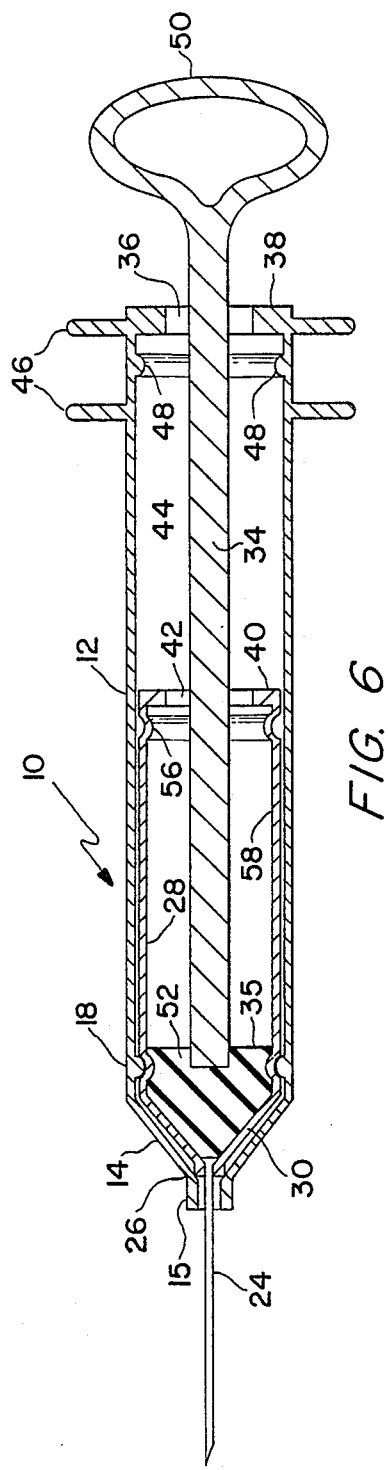
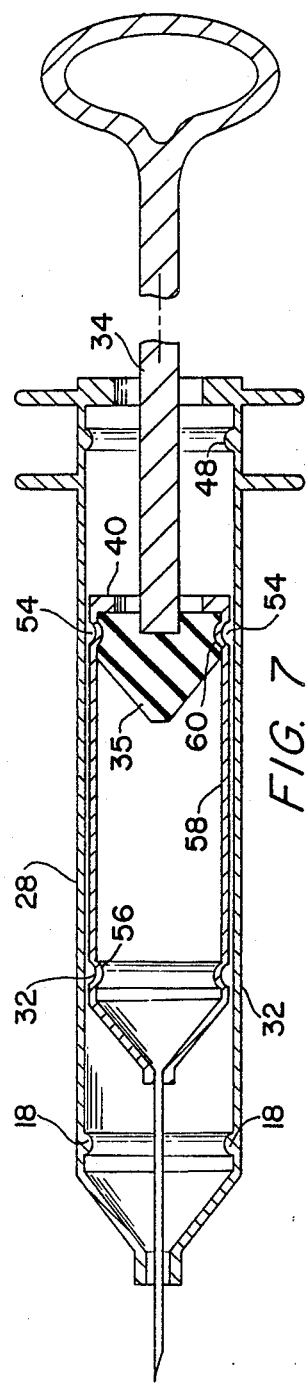
FIG. 6
FIG. 7

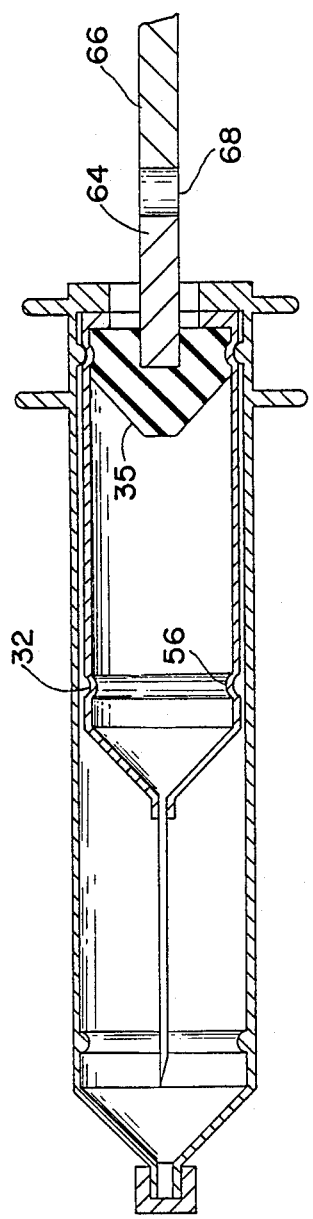
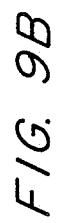
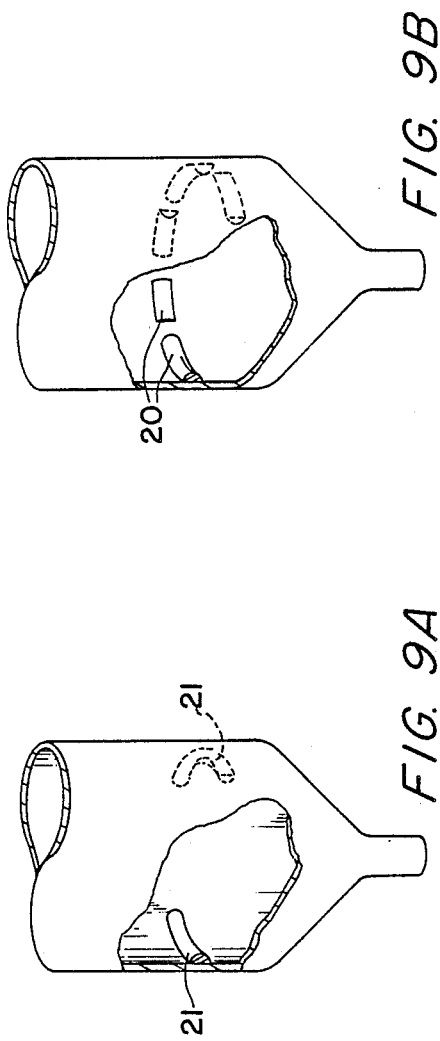
FIG. 8
FIG. 9B
FIG. 9A

SYRINGE

This is a divisional of co-pending application Ser. No. 07/259,709 filed on Oct. 19, 1988 now U.S. Pat. No. 4,915,699.

BACKGROUND OF THE INVENTION

1. Field of the Invention

This invention relates to a syringe. More particularly, this invention relates to a syringe having a retractable needle which can be releasably locked in operational and non-operational position.

2. Description of the Prior Art

The concern over protecting medical personnel from coming into contact with infectious diseases by contact with contaminated needles has led to the development of syringes with retractable needles. The recent concern over the avoidance of being infected with the AIDS virus has led to even a greater importance being placed in the use of retractable needles.

U.S. Pat. Nos. 4,650,468 and 4,643,199 are examples of syringes which have been developed so as to allow for a potentially infectious needle to be withdrawn into the syringe's interior after use.

Each of the above two United States Patents involve the formation of grooves in an inner cylindrical member and the formation of locking lugs on an outer cylindrical member. To position the needle in an operational position, the inner member is first rotated such that the lugs of the outer member becomes disengaged from a first locking section of the inner member's grooves. Subsequently, the outer member is drawn along a straight line section of the inner member's grooves. Thereafter, the inner member is again rotated with respect to the outer member until the lugs of the outer member become locked within a second locking section of the inner member's grooves. To retract the needle attached to the inner member after use, the same procedure is followed only in reverse.

Thus, in the above two patents there is a requirement that the grooves and lugs be placed in alignment during the process of locking the needle into operational position and during the process of retracting the needle after use. This alignment requirement presents a problem when quick positioning of the needle is essential such as in an emergency situation. There also exists the possibility that initial problems in alignment can result in the user becoming panicked which could lead to even further time delays.

Moreover, as the various components of the syringe are likely to be rotated with respect to one another, there also exists the problem of unwanted release. That is, during the use of the syringe the inner and outer members might inadvertently become aligned along the straight groove portion and create an accident due to undesirable movement of the needle.

U.S. Pat. Nos. 4,507,117 and 4,675,005 illustrate syringes having retractable needles which are releasably connected directly to the plunger by way of rotation. Accordingly, these syringes suffer the same problems noted above with regard to rotative attachment and detachment.

U.S. Pat. No. 4,692,156 to Haller shows a retractable needle which is locked directly onto the sealing plug of a plunger. Haller, in one embodiment utilizes a "snapping" connection between the needle and plug. This "snapping" connection is essentially non-detachable and thus Haller provides a one shot device. That is, inadvertent attachment before use cannot be remedied. Therefore, either direct contact is made with the needle to separate the needle from attachment with the plug or the syringe is discarded as useless.

SUMMARY OF THE INVENTION

An object of the present invention is to avoid the aforementioned problems associated with the prior art and to provide a syringe which, among others, is safe; quickly, securely and easily placed into operational and non-operational position, and inexpensive to manufacture.

In so providing, the invention features an outer preferably cylindrical casing and an inner chamber positioned within the interior of the outer casing. The outer casing includes a conically converging front end and an essentially open end. The outer casing is elongated and includes a central axis. A hole is formed at the tip of the front end of the outer casing with the center of the hole lying on the central axis.

The inner chamber is somewhat shorter in length than the outer casing and the inner chamber includes a conically converging front end which converges to a tipped end. The conically converging front end of the inner chamber is adapted to nestle within the conically converging front end of the outer casing when the inner chamber is placed at the forefront of the outer casing.

Releasably or permanently attached to the tipped end of the inner chamber is a needle or cannula which extends a distance out away from the inner chamber and is adapted to slide through the hole in the tipped end of the outer casing.

A plunger having a sealing plug attached to one of its ends is adapted to slide within the interior of the inner chamber. To prevent the plug from being withdrawn out of the chamber, inwardly extending abutments are formed along the open end of the inner chamber so as to come in contact with the sealing plug upon withdrawal of the plunger.

In addition, inwardly extending stops are formed along the essentially open end of the outer casing so as to prevent the inner chamber from being withdrawn from the interior of the outer casing.

The inner chamber and outer casing are formed such that the frictional contact between the interior surface of the outer casing and the exterior surface of the inner chamber makes it difficult to slide the inner chamber along the length of the outer casing. On the other hand, the sealing plug is made to easily slide within the interior of the inner chamber or at least the frictional contact between the exterior of the plug and the interior of the inner chamber is less than that between the contacting surface of the inner chamber and outer casing.

The syringe of the present invention is formed using any conventional apparatus such as, for example, extrusion apparatus, injection mold apparatus, or the like.

The higher frictional contact between the inner chamber and outer casing is preferably brought about by a force fitting arrangment between the inner chamber and outer casing. That is, the allowance between the cross-sectional exterior of the inner chamber and the cross-sectional interior of the outer casing is virturally non-existent or such that an interference fit exists therebetween. This fit makes it relatively difficult to move the inner chamber with respect to the outer casing.

If necessary, further enhancement of the frictional contact between the two contacting surfaces can be achieved by utilization of a rough surface either for the exterior of the inner chamber, the interior of the outer casing, or both.

The materials contemplated for use in the present invention are the materials utilized for conventional syringes especially those of the disposable type. The sealing plug is also preferably formed of conventional materials with a relatively hard plastic material with a low coefficient of friction being preferred. The tolerance space between the sealing plug and the inner chamber is preferably made as high as possible without destroying the sealing function of the plug.

In storage position, the rear of the inner chamber is essentially coincident with the rear, or essentially open, end of the outer casing. That is, the essentially open end of the inner chamber is in abutment with the inwardly extending stops positioned at the outer casing's open end.

To place the syringe in operational position from its storage position, the plunger with attached sealing plug is pushed forward within the inner chamber until the sealing plug makes contact with the forefront of the inner chamber. An increase in forward force on the plunger allows for the static frictional bond between the inner chamber and outer casing to be released. The release of the frictional bond between the inner chamber and outer casing allows for the inner chamber to be moved to an operational position at the forefront of the outer casing.

Because the frictional contact between the inner chamber and outer casing is greater than that between the sealing plug and inner chamber, fluid can be drawn into the inner chamber as the sealing plug is drawn away from the forefront of the inner chamber without having the inner chamber move with reespect to the outer casing. Additionally, fluid can be forced back through the needle by pushing the sealing plug back towards the forefront of the inner chamber without releasing the frictional bond between the inner chamber and outer casing. Again, this is made possible by the differences in frictional contact between the respective contacting surfaces of the inner chamber, sealing plug and outer casing.

After use, the needle can be withdrawn into a retracted position. This is achieved by drawing the plug away from the forefront of the inner chamber until the plug makes contact with the inwardly extending abutments at the rearward end of the inner chamber. An increased pull on the plunger will act to break the static frictional bond between the inner chamber and outer casing and allow for the inner chamber to be moved rearwardly to a position previously referred to as a storage position.

The inner chamber is maintained in the storage position due to the frictional contact between the inner chamber and outer casing. Additionally, the needle is maintained in a retracted position due to its securement to the inner chamber.

In its retracted position, the needle is encompassed entirely by the outer casing such that an operator does not come in contact with a potentially contaminated needle. This necessitates that the outer casing is of a length that is greater than the needle and inner chamber combined. Preferably, the inner chamber and outer casing have essentially a uniform cross-sesction along their respective lengths except for the converging front area of each. Alternatively, the cross-section fo the outer casing can taper inwardly near its open end and-/or conically converging front end. Such tapering at or just before the converging front end or the open end, further ensures that the outer casing and inner chamber will enter into a secure interference fit when the needle is placed in an operative position and/or a retracted position.

Moreover, it is also contemplated in the present invention that frictional strips be placed on the outer casing near the forward and rearward ends of the syringe such that a higher frictional bond is assured when the inner chamber is in an operational position or in a storage position.

In a further embodiment of the present invention, rather than utilizing an interference fit to releasably secure the inner chamber to the outer casing, one or more knobs are formed on either the inner chamber or the outer casing. The knobs are adapted to releasably lock within corresponding grooves or recesses formed in either the inner chamber or outer casing depending on which of the two does not already include the knob or knobs.

In such an arrangment, one or more knobs can be positioned to extend inwardly off the interior surface at the forward end of the outer casing while a corresponding groove (or grooves) is formed in the exterior surface of the inner chamber. To avoid any type of rotative alignment, the groove preferably extends about a majority of the inner chamber and more preferably, about the entire cross-sectional surface of the inner chamber.

With such an arrangement, the same steps for placing the needle into operational position and then retracting it are carried out. Refer than relying on an interference or friction fit to releasably lock the inner chamber in position with respect to the outer casing, the knob or knobs and corresponding groove or grooves provide the releasable locking arrangement. That is, grooves are formed in the exterior of the inner chamber near both the front and rear of the inner chamber. Moreover, one or more knobs are formed on the interior of the casing near the forward and rearward end of the outer casing. Thus, when the inner chamber is pushed to the forefront of the outer casing, the forwardmost knob or knobs enter into a releasable locking engagement with the forwardmost groove or grooves in the inner chamber. Similarly, when the inner chamber is retracted to its storage position, the rearward groove or grooves receive the rearward knob or knobs formed on the outer casing.

It is also contemplated that the grooves be formed within the interior of the outer casing and the knob or knobs on the exterior surface of the inner chamber. In addition, the present invention contemplates the forwardmost groove being formed in the inner chamber at its forward end and the rearwardmost groove being formed in the outer caseing at its rearward end or vice versa.

Rather than utilizing one or more knobs, it is also contemplated that a continuous or intermittent ridge be formed instend of the knob or knobs.

The present invention contemplates the use of a non-continuous groove or recess as forming part of the releasable locking means. However, such non-continuous grooves should be of a length which ensures that undue rotation to insert a knob or intermittent ridge is not required. For instance, when utilizing an intermittent ridge, a matching intermittent groove may be utilized. Although some rotation may be required to place the intermittent ridge within the intermittent groove, such rotation will be minimal (if required at all) and thus not as problematic as the rotation required in the prior art syringe locking devices.

Accordingly, it is evident that the present inventiuon can be placed quickly into operational position and quickly into a retracted position by simple movement of the plunger without rotation or, for one embodiment, only slight rotation at most. Moreover, the invention, with its few components, can be manufactured at low costs.

BRIEF DESCRIPTION OF THE DRAWINGS

Other advantages and improvements over the prior art will become more apparent from the description made hereinbelow with reference to the accompanying drawings in which:

FIG. 1 represents a cross-sectional partially cut away view of the invention with the inner chamber in storage position.

FIG. 2 represents a cross-sectional view of the invention with the inner chamber in operational position.

FIG. 6 represents a cross-sectional view of the embodiment of FIG. 5 with the needle in operational position.

FIG. 7 represents a cross-sectional view of the embodiment of FIG. 5 with the needle in-between being released from operational position and being locked in storage position.

FIG. 8 represents a cross-sectional view of still another embodiment of the present invention.

FIGS. 9A and 9B represent cut away views of the spaced knobs and intermittent ridges formed in the outer casing.

DETAILED DESCRIPTION OF THE PREFERRED EMBODIMENTS

Figure 4:
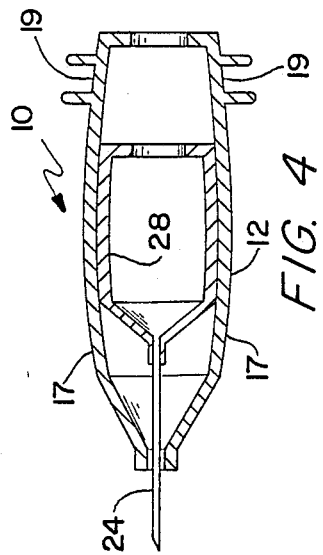
FIG. 4 represents a cross-sectional view of another embodiment of the invention with the plunger and sealing plug removed for clarity.

FIG. 1 illustrates a cross-sectional view of a preferred embodiment of the invention. In FIG. 1 a syringe 10 is shown to have outer casing 12 which is preferably formed of a transparent or translucent plastic material. Outer casing 12 is generally cylindrical is shape and includes a conically converging end 14 which extends into protruding tip 15.

Referring again to FIG. 1, the protruding tip 15 of the outer casing 12 is covered by cap 22. Cap 22 can be used to protect the needle from contaminates during storage and prior to use. The cap can either be frictionally fitted onto protruding tip 15 or there can be a threaded arrangement between the cap 22 and protruding tip 15. After use, the cap 22 can either be returned or left off since the needle 24 will remain in a fixed retracted position as will be explained hereafter. Alternatively, while the needle is in storage position, the protruding tip can be left open or covered by a plastic wrap or the like which can be punctured by the needle when the needle is placed into operational position.

Needle 24 is securely fixed to, or releasably secured (i.e. a threaded engagement) to, protruding tip 26 of the inner chamber 28. Inner chamber 28 has a converging conical end 30 which slopes inwardly at about the same incline as converging end 14. The exterior diameter of inner chamber 28 is such that an interference fit exists between the inner chamber and outer casing. In addition, the tolerances are such that there exists an arrangement between the inner chamber and outer casing which prevents one from sliding with respect to the other until a sufficient pull or push is applied to the inner chamber.

As illustrated in FIG. 2, outer casing 12 has a second, essentially open end 36 which is surrounded by stop means 38. Stop means 38 is adapted to come into engagment with abutment means 40 formed at the open end 42 of inner chamber 28 such that the inner chamber is non-removable from the interior 44 of the outer 12. Outer casing 12 further includes finger extensions 46. However, the invention should not be considered limited to the use of finger extensions 46 as any other suitable gripping means would be considered adequate for the purpose of the invention.

FIGS. 1 and 2 also reveal that the exterior and interior surfaces of the inner chamber and the interior surface of the outer casing are essentially devoid of any interruptions or protrusions from their open end (excluding the stop and abuttment means 38, 40) to their front end.

In FIGS. 1 and 2, a plunger 34 with attached sealing plug 35 extends into the inner chamber and outer casing such that sealing plug 35 is within the interior of both the inner chamber and outer casing. The plunger is of a length which allows the sealing plug 35 to extend to the tipped end of the outer casing before handle 50 comes in contact with stop means 38. Rather than handle 50, various conventional thumb positioners are also possible including, for example, a circular platform secured to the end of shaft 33 (FIG. 2).

Sealing plug 35 is preferably formed of a material which has a low coeffcient of friction such as a nylon material. The plug is dimensioned so as to be easily slidable along the interior of inner chamber 28. In addition the sealing plug is dimensioned such that its rearward wall 52 abuts abutment means 40 resulting in the sealing plug being retained within the interior of the inner chamber.

The interference fit arrangement between the exterior of the inner chamber 28 and the interior of the outer casing 12 as well as the type of materils chosen, allows for the achievement of a relatively high value in the force required to move the inner chamber with respect to the outer casing. This can be seen in the equation $F_1 = X_1 W_1$ where $F_1$ equals the force required to initiate movement between the inner chamber and outer casing; $X_1$ equals the coefficient of static friction between the two contacting surfaces of the inner chamber and outer casing; and $W_1$ equals the force pressing the two surfaces together. Thus, the interference fit between the inner chamber and outer casing allows for a relatively high force necessary to break the frictional bond between the inner chamber and outer casing. It is also noted that the term "interference fit" is used herein in the manner commonly used in the art as exemplified by page 466 of *Materials and Processes in Manufacturing*; by E. Paul DeGarmo, 1979.

The force, $F_2$, required to initiate movement between the sealing plug and interior of the inner chamber is of a value lesser than that of $F_1$. This allows the inner chamber and outer casing to remain stationary with respect to one another as the fluid is drawn in and ejected out of inner chamber 28.

For the contact between the exterior of the sealing plug 35 and the interior of the inner chamber 28, the equation is $F_2 = X_2 W_2$. As the force pressing the two surfaces together, $W_2$, will be fairly high (although not necessarily higher than that between the inner chamber and outer casing) in order to maintain the sealing contact between the sealing plug 35 and inner chamber 28, preferably the coefficient of static friction $X_2$ will be lower than that of $X_1$. For example, a sealing plug of nylon material against a smooth plastic surface for the inner chamber would result in a relatively low $X_2$ and thus a relatively low $F_2$.

The invention is not limited, however, to having $X_2$ less than $X_1$, but rather $F_2$ lower than $F_1$. Thus, so long as the product of ($X_2 \times W_2$) is lesser than ($X_1 \times W_1$) the requirements of the invention will be met.

To ensure even a greater difference between $F_2$ and $F_1$, various means are available. For instance, a roughening of either the exterior surface of the inner chamber 28, the interior surface of the outer casing 12, or both, would result in a higher $X_1$ value and therefore even a higher $F_1$ value. This means of increasing the difference between $F_1$ and $F_2$ is especially suitable for disposable syringes as a wearing of the roughened surface or surfaces will not present a problem. The roughening of the two surfaces can be achieved in any conventional manner including the well known moulding techniques which result in a roughened surface.

Figure 3:
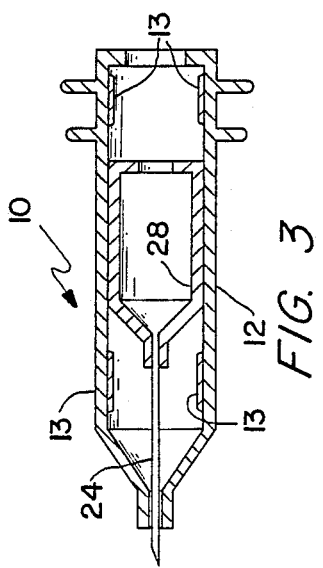
FIG. 3 represents a cross-sectional view of an alternate embodiment of the invention with the plunger and sealing plug removed from clarity.

FIG. 3 reveals another way in which the ratio of the value of $F_1$ to $F_2$ can be increased. In FIG. 3, outer casing 12 has formed near its forward and rearward ends friction increasing means 13. Friction increasing means 13 can be a single or a plurality of strips of high friction coefficient material which are secured to the interior of outer casing 12. The friction increasing means act to increase the value of $X_1$ in the equation $F_1 = X_1 W_1$. Depending on the thickness of the friction increasing means utilized, $W_1$ may also be increased. However, to avoid blockage problems, the friction enhancing means 13 are preferably very thin in nature or at least are provided with fore and aft ramp to assist in the passage of the inner chamber 28 thereover. A non-limiting example of a suitable friction increasing means for the invention would be a roughened synthetic or natural rubber strip (or strips) adhesively secured to the outer casing's interior.

FIG. 4 features an alternative embodiment of the present invention wherein the outer casing includes tapering ends 17, 19 which preferably taper slightly inwardly from near the mid portion of the outer casing to just before the conically converging portion 14 of the front end and just before the open end 36. The tapering ends 17, 19 would act to increase the value $W_1$ in the equation $F_1 = X_1 W_1$ thus further ensuring that the value of $F_1$ sufficiently exceeds the value of $F_2$.

In use, the syringe is taken out of the storage position of FIG. 1 and placed into the operating position of FIG. 2. The frictional locking engagement between the outer casing 12 and the inner chamber 28, as depicted in FIG. 2, is such that a withdrawal of plunger 34 with attached plug 35 is possible without destroying the locking engagement between the inner chamber and outer casing. Hence, fluid can be drawn though needle 24 and into inner chamber 28 in a conventional manner.

Once the appropriate amount of fluid is withdrawn the plunger can be pushed forward to cause the fluid to pass out through the needle.

After use, the needle can be withdrawn into the interior of the out casing by withdrawing the plunger 34 until the rearward wall 52 of sealing plug 35 comes in contact with abutment means 40, whereby a further withdrawal of the plunger results in the release of the frictional locking engagement between the inner chamber 28 and outer casing 12. The plunger 34 is then further withdrawn against the lower kinetic frictional force which exists between the moving inner chamber and outer casing until the abutment means 40 and stop means 38 come into contact. In this position, the needle 24 attached to inner chamber 28 lies completely within the interior 44 of outer casing 12 (i.e., the storage position of FIG. 1).

Figure 5:
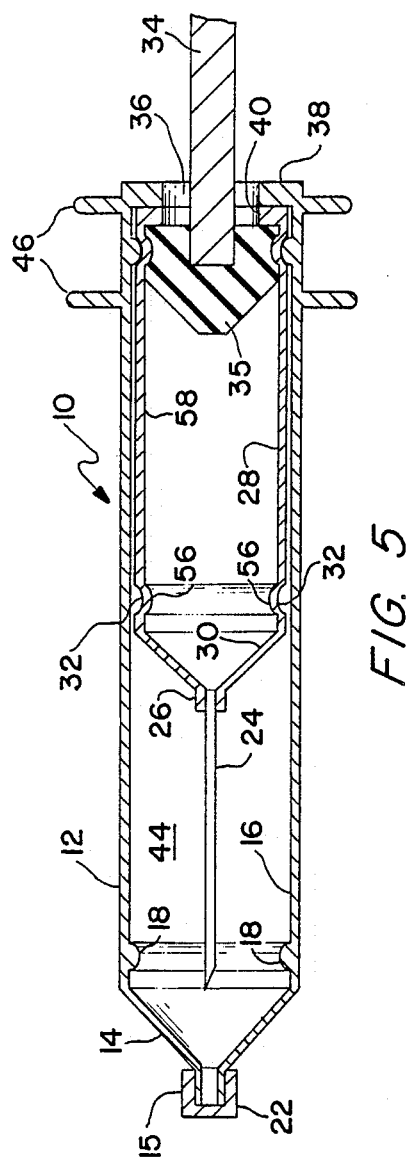
FIG. 5 represents a cross-sectional view of yet another embodiment of the invention with the needle in a storage position.

FIG. 5 illustrates a cross-sectional view of another embodiment of the invention. Formed on the interior surface 16 of outer casing 12 is a continuous circumferential ridge 18 which preferably extends about the entire internal circumference of the outer casing 12. The ridge 18 extends out away from the inner surface 16 of the outer casing a distance preferably failing within the range of about 0.25 mm to 2.0 mm.

Alternatively, rather than a single continuous ridge, a non-continuous, intermittent ridge 20 (FIG. 9B) may be utilized with the intermittent ridge 20 preferably extending about the entire circumference of the interior surface of the outer casing.

Near the converging end 30 of inner chamber 28 is a circumferential recess 32 which preferably extends about the entire external circumference of inner chamber 28. Recess 32 is of a depth which is about the same as the distance ridge 18 extends out away from the interior surface of the outer casing. Alternatively, the recess can be intermittent so as to compliment intermittent ridge 20. However, this arrangement might require slight rotative alignment and thus, from a rotation requirement standpoint, is not as preferable as a continuous groove or recess.

The recess and the slightly flexible nature of the inner chamber 28 allows for a releasable locking arrangement between the inner chamber 28 and outer casing 12 once the inner chamber is slid over the continuous or intermittent ridge 18, 20. Also, because of the use of this type of releasable locking arrangement, an interference fit between the inner chamber 28 and outer casing 12 is not necessary. When the forwardmost locking arrangement is activated, the needle 24 is in operational position extending out through a hole in protruding tip 15, as shown in FIG. 6.

As illustrated in FIG. 9A, rather than a continuous or intermittent ridge (18,20) one or more knobs 21 may be utilized. FIG. 9A shows two knobs 21 diametrically opposed from one another. To avoid alignment requirements the groove or recess preferably extends about the entire periphery of the exterior surface of the inner chamber. Although not as desirable, the invention also contemplates the use of one or more grooves formed to compliment the one or more knobs. The number of knobs 21 and their peripheral length and spacing depends, in part, on such characteristics as the material forming the inner chamber and outer casing, the clearance space provided for between the exterior of the inner chamber and the interior of the outer casing, the height of the knobs and the depth of the recess. The arrangement of the knobs 21 and recess must be such that the locking engagement remains intact while the sealing plug 35 slides within the interior of the inner chamber.

The invention also contemplates the reversal of the positioning of the ridges or knobs and the grooves or recesses. For example, the grooves formed on the interior surface of the outer casing and the ridges formed on the exterior surface of the inner chamber. The exterior diameter of inner chamber 28 is somewhat less than the diameter of the internal surface 16 of outer casing 12 due to the non-necessity of an interference fit. For instance, a diameter of about 25 mm for the interior surface of outer casing 12 and an exterior diameter of about 24.5 mm for the inner chamber 28 would be suitable. For such diameters the ridge 18, 20 or knobs 21 would preferably extend inwardly about 1 mm. An increased length in the ridge 18,20 or knobs, say up to 2 mm, would allow for even a greater allowance of about 1.5 mm between the inner chamber and outer casing. Matching cross-sectional configurations of shapes other than cylindrical shapes for the inner chamber and outer casing are also possible but cylindrical cross-sections are preferred. In addition, the overall size of the syringe of the present invention is not critical and thus the syringe can be made in any appropriate size.

Figure 10A:
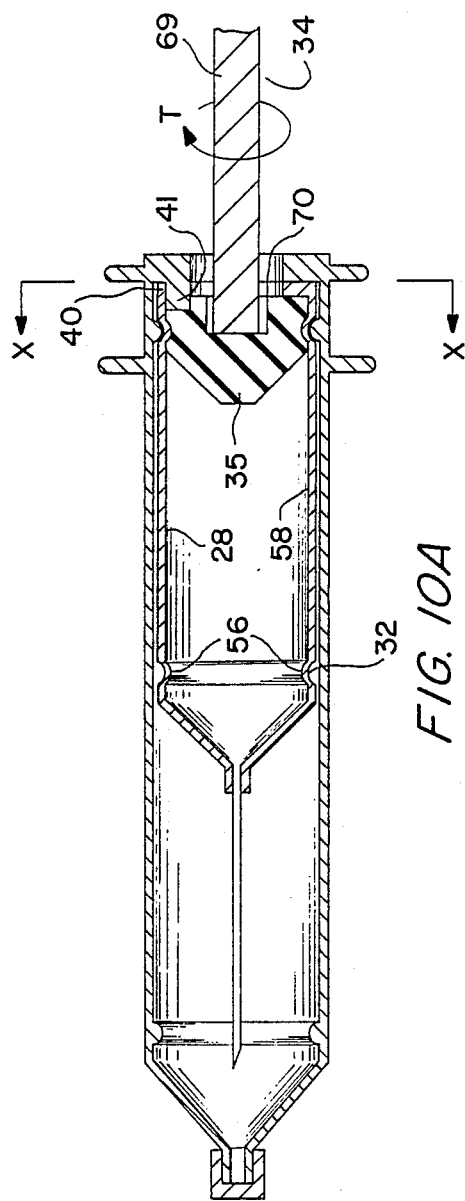
FIG. 10A represents a cross-sectional view of an alternate embodiment of the present invention.

As best depicted in FIG. 7, groove 54 is formed within the inner chamber's exterior surface. Groove 54 is adapted to lockingly receive the continuous or intermittent ridge 48 as shown in FIGS. 5, 6 and 10A. The location of the locking arrangement between the inner chamber and outer casing near the open end of each, is such that the abutment means 40 nestles against the interior surface of stop means 38.

The groove 54 and recess 32 in the inner chamber result in inward protrusions 56 being formed on the interior surface 58 of inner chamber 28. In one embodiment of the invention, the sealing plug 35 includes a circumferential groove 60 (FIG. 7) which can be placed in locking engagement with inward protrusions 56 either at the tipped end or open end of the inner chamber. Alternatively, a sealing plug with a non-grooved exterior surface may be utilized.

It is also contemplated that the inner chamber be made thick enough such that grooves 54 can be formed without inward extensions 56 being formed. This would result in the sealing plug not becoming lockingly engaged within the inner chamber but would allow for the appropriate locking engagements between the inner chamber and outer casing.

In use, the syringe is taken out of the storage position of FIG. 5 and placed into the operating position of FIG. 6. The locking engagement between the outer casing 12 and the inner chamber 28, as depicted in FIG. 6, is such that a withdrawal of plunger 34 with attached plug 35 is possible without destroying the locking engagement between the inner chamber and outer casing. Hence, fluid can be drawn through needle 24 and into inner chamber 28 in a conventional manner.

Once the appropriate amount of fluid is withdrawn, the plunger can be pushed forward to cause the fluid to pass out through the needle.

After use, the needle can be withdrawn into the interior of the outer casing by following the procedure illustrated in FIG. 7. In FIG. 7, the plunger is withdrawn until the rearward wall 52 of sealing plug 35 comes in contact with abutment means 40, whereby a further withdrawal of the plunger results in the release of the locking engagement between continuous or intermittent recess 32 and ridge 18.

The plunger 34 and attached inner chamber are then further withdrawn until groove 54 becomes lockingly engaged with continuous or intermittent ridge 48 as illustrated in FIG. 5. In this position the inner chamber is fixed just within the open end 36 of outer casing 12. In addition, sealing plug 35 can be placed in locking engagement with inner chamber 28 at the point of contact between circumferential groove 60 (FIG. 7) and inward protrusion 56 (FIG. 6).

FIG. 8 shows another embodiment of the present invention wherein pluger 34 has a first portion 64 preferably adhesively fixed within a bore formed in the rearward wall of plug 35. Plunger 34 further includes a second portion 66 which is releasably secured to attachment means 68. In a preferred embodiment, attachment means 68 includes a threaded extension on one of the two portions which is received within a threaded socket of the other portion. The length of first portion 64 is such that it can be gripped as second portion 66 is detached. Such an arrangement saves storage and diposal space by allowing the second portion of the elongated plunger with handle to be separated from the first portion attached to the sealing plug. Once the second portion is discarded after use and the first portion 64 with attached plug is placed within the inner chamber's interior, it becomes more difficult for the sealing plug to be pushed forward to disengage the inner chamber from the outer casing. That is, the length of plug 35 and first portion 64 is less than the length of the inner chamber's interior. Accordingly, inadvertent displacement of the needle is less likely which alleviates the requirements for a cap in most instances.

Figure 10B:
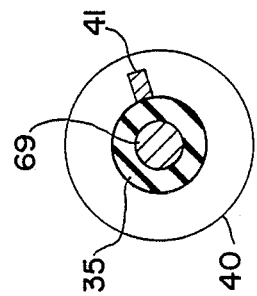
FIG. 10B represents a cross-sectional view along line X—X of FIG. 10A.

An alternative embodiment is shown in FIGS. 10A and 10B. This embodiment is also directed at preventing the needle from inadvertently being placed in an operational position after use. In the embodiment of FIGS. 10A and 10B stop means 40 includes key 41 which extends off of outer casing 12 toward the tipped end of the inner chamber. Key 41 is adapted to be received within a depression formed in the rearward wall of plug 35 and a slot formed in abutment means 40. In addition, the sealing plug 35 is attached to shaft 69 of the plunger, by way of threaded engagement 70.

Key 41, when placed within the depression in the rearward wall of plug 35, enables shaft 69 to be disengaged from its threaded attachement with the plug's threaded hole 70 by fixing the plug in place as torque T is provided on shaft 69.

While the invention has been described in conjunction with the preferred apecific embodiments thereof, it will be understood that the description is intended to illustrate and not limit the scope of the invention which is defined by the following appended claims. Moreover, although the following description makes reference to specific materials of construction, the present invention can be formed of any material in the art which achieves the requirements set forth in the description.

What is claimed is:

1. A syringe, comprising:
   (a) an elongated outer casing having a forward end, a rearward end, an exterior surface and an interior surface with said interior surface defining an interior space;
   (b) an elongated inner chamber slidably received within the interior space in said outer casing, said inner chamber having a forward end, a rearward end, and exterior surface and an interior surface with said interior surface defining a hollow interior, and said inner chamber having abutment means at the rearward end of said inner chamber;

(c) a plunger with a sealing plug attached to one end, said sealing plug adapted to slide within the hollow interior of said inner chamber between the forward end and said abutment means at the rearward end of said inner chamber such that said inner chamber can be drawn rearwardly within said outer casing;

(d) first attachment means for releasably attaching said inner chamber to said outer chamber such that the forward end of said inner chamber is essentially coincident with the forward end of said outer casing, said first attachment means including at least one knob extending peripherally about a portion of the exterior surface of said inner chamber and said first attachment means further including a recess formed within said outer casing which extends about the periphery of the interior surface of said outer casing and is adapted to releasably lock said at least one knob.

2. A syringe as recited in claim 1 further comprising a needle in attachment with the forward end of said inner chamber and adapted to extend through a hole formed in the forward end of said outer casing.

3. A syringe as recited in claim 1 further comprising second attachment means for releasably attaching said inner chamber to said outer chamber such that the rearward end of said inner chamber is essentially coincident with the rearward end of said outer casing.

4. A syringe as recited in claim 3 wherein said second attachment means includes at least one knob extending peripherally about a portion of the interior surface of said outer casing and second attachment means further including a groove formed within the exterior surface of said inner chamber which is adapted to releasably lock said at least one knob of said second attachment means.

5. A syringe as recited in claim 3 wherein said second attachment means includes at least one knob extending peripherally about a portion of the exterior surface of said inner chamber and said second attachment means further including a groove formed within the interior surface of said outer casing which is adapted to releasably lock said at least one knob of said second attachment means.

6. A syringe as recited in claim 1 wherein said inner chamber and said outer casing are formed of a plastic material.

7. A syringe as recited in claim 1 wherein said abutment means prevents the complete withdrawal of said sealing plug from the hollow interior of said inner chamber and said outer casing includes stop means for preventing the complete withdrawal of the inner chamber from the interior space of said outer casing.

8. A syringe as recited in claim 1 wherein said inner chamber and outer casing are essentially circular in cross-section.

9. A syringe, comprising:
(a) an outer casing having a forward end, a rearward end, an exterior surface and an interior surface with said interior surface defining an interior space;
(b) an inner chamber slideably received within the interior space in said outer casing, said inner chamber having a forward end, a rearward end, an exterior surface and an inner surface with said interior surface defining a hollow interior, and said inner chamber having abutment means at the rearward end of said inner chamber;

(c) a plunger with a sealing plug attached to one end, said sealing plug being slideably received within the hollow interior of said inner chamber between the forward end and said abutment means at the rearward end of said inner chamber such that said inner chamber can be drawn rearwardly within said casing;

(d) a needle in attachment with the forward end of said inner chamber and adapted to extend through a hole formed in the forward end of said outer casing;

(e) first attachment means for releasably attaching said inner chamber to said outer chamber such that the forward end of said inner chamber is essentially coincident with the forward end of said outer casing, said first attachment means including at least one ridge extending peripherally about the interior surface of said outer casing and said first attachment means further including a recess formed within the exterior surface of inner chamber casing which is adapted to releasably receive said at least one ridge and lock together said inner chamber and outer casing.

10. A syringe as recited in claim 9 wherein said ridge is continuous and extends about the entire periphery of the interior surface of said outer casing.

11. A syringe as recited in claim 9 wherein said ridge is intermittent and extends intermittently about the entire periphery of the interior surface of said outer casing.

12. A syringe as recited in claim 9 wherein said needle is releasably secured to the forward end of said inner chamber.

13. A syringe as recited in claim 9 further comprising second attachment means for releasably attaching said inner chamber to said outer chamber such that the rearward end of said inner chamber is essentially coincident with the rearward end of said outer casing.

14. A syringe is recited in claim 13 wherein said second attachment means includes a ridge and said ridge is continuous and extends about the entire periphery of the exterior surface of said inner chamber.

15. A syringe as recited in claim 13 wherein said second attachment means includes a ridge and said ridge is intermittent and extends intermittently about the entire periphery of the exterior surface of said inner chamber.

16. A syringe as recited in claim 13 wherein said second attachment means includes a ridge extending peripherally about the interior surface of said outer casing and said second attachment means further including a groove formed within the exterior surface of said inner chamber into which said ridge of said second attachment means is releasably received when said second attachment means is in an attached state.

17. A syringe as recited in claim 16 wherein said ridge of said second attachment means is continuous and extends about the entire periphery of the inner surface of said outer casing.

18. A syringe as recited in claim 16 wherein said ridge of said second attachment means is intermittent and extends intermittently about the entire periphery of the inner surface of said outer casing.

19. A syringe as recited in claim 9 wherein said ridge extends continuously about a majority of the periphery of the interior surface of said outer casing.

20. A syringe as recited in claim 9 wherein said ridge extends intermittently about a majority of the periphery of the interior surface of said outer casing.

21. A syringe as recited in claim 9 wherein said inner chamber and said outer casing are formed of a plastic material.

22. A syringe as recited in claim 9 wherein said abutment means prevents the complete withdrawal of said sealing plug from said inner chamber and said outer casing has stop means for preventing the complete withdrawal of said inner chamber from said outer casing.

23. A syringe as recited in claim 9 wherein said inner chamber and outer casing are essentially circular in cross-section.

24. A syringe assembly, comprising:
an elongated outer casing having a longitudinal axis, a forward end, a rearward end, an exterior surface and an interior surface with said interior surface defining an interior space;
an elongated inner chamber slideably received within the interior space in said outer casing along said longitudinal axis, said inner chamber having a forward end, a rearward end, an exterior surface and an interior surface with said interior surface defining a hollow interior, and said inner chamber including an inwardly extending flange at said rearward end of said inner chamber;
a plunger with a sealing plug attached to one end, said sealing plug adapted to slide within the hollow interior of said inner chamber between the forward and rearward ends of said inner chamber, and said sealing plug being dimensioned such that said sealing plug abuts said flange upon said plunger being drawn rearwardly;
first attachment means for releasably attaching said inner chamber to said outer casing, such that at least the forward end of said inner chamber is adapted to be releasably locked in a position essentially conincident with the forward end of said outer casing;
second attachment means for releasably attaching said inner chamber to said outer casing with said second attachment means being such that, when said second attachment means is in an attachment mode, the rearward end of said inner chamber is essentially coincident with the rearward end of said outer casing; and
said first attachment means including at least one knob extending peripherally about a portion of the interior surface of said outer casing, said first attachment means further including at least one recess formed within said inner chamber which extends about the periphery of the exterior surface of said inner chamber and is adapted to releasably lock in place said at least one knob, and said second attachment means including at least one knob extending peripherally about a portion of the interior surface of said outer casing and said second attachment means further including a groove formed within said exterior surface of said inner chamber which is adapted to releasably lock in place said at least one knob of said second attachment means.

* * * * *